United States Patent [19]
Lee et al.

[11] Patent Number: 5,480,403
[45] Date of Patent: Jan. 2, 1996

[54] SUTURE ANCHORING DEVICE AND METHOD

[75] Inventors: Daniel R. Lee, Warsaw; Thomas W. Sander, Winona Lake, both of Ind.

[73] Assignee: United States Surgical Corporation, Norwalk, Conn.

[21] Appl. No.: 331,241

[22] Filed: Oct. 28, 1994

Related U.S. Application Data

[63] Continuation of Ser. No. 284,731, Aug. 2, 1994, abandoned, which is a continuation of Ser. No. 214,042, Jan. 28, 1994, abandoned, which is a continuation of Ser. No. 898,799, Jun. 15, 1992, abandoned, which is a continuation-in-part of Ser. No. 673,953, Mar. 22, 1991, abandoned.

[51] Int. Cl.$^6$ .......................................................... A61F 5/04
[52] U.S. Cl. ................................................ 606/72; 606/63
[58] Field of Search .................................. 606/60, 63, 72, 606/73, 74, 76, 138, 139, 144, 148, 224, 225, 226, 232

[56] References Cited

U.S. PATENT DOCUMENTS

| | | |
|---|---|---|
| 2,381,050 | 8/1945 | Hardinge . |
| 2,490,364 | 12/1949 | Livingston . |
| 2,699,774 | 1/1955 | Livingston . |
| 3,910,281 | 10/1975 | Kletschka et al. . |
| 4,351,069 | 9/1982 | Ballintyn et al. . |
| 4,519,100 | 5/1985 | Wills et al. . |
| 4,520,511 | 6/1985 | Gianezio et al. . |
| 4,539,981 | 9/1985 | Tunc ................................. 606/72 X |
| 4,550,449 | 11/1985 | Tunc . |
| 4,590,928 | 5/1986 | Hunt et al. ................................. 606/72 |
| 4,590,930 | 5/1986 | Kurth et al. . |

(List continued on next page.)

FOREIGN PATENT DOCUMENTS

| | | |
|---|---|---|
| 0077868 | 5/1983 | European Pat. Off. . |
| 0241240 | 10/1987 | European Pat. Off. . |
| 0464480 | 1/1992 | European Pat. Off. . |
| 0464479 | 1/1992 | European Pat. Off. . |
| 0465910 | 1/1992 | European Pat. Off. . |
| 2622430 | 5/1989 | France . |
| 3445738 | 6/1986 | Germany . |
| 4106823 | 6/1992 | Germany . |
| 584855 | 12/1977 | U.S.S.R. ................................. 606/73 |
| 2084468 | 4/1982 | United Kingdom . |
| 0232049 | 8/1987 | WIPO . |
| 8909030 | 10/1989 | WIPO . |
| 8910096 | 11/1989 | WIPO . |
| WO9204874 | 3/1992 | WIPO . |
| 9308747 | 5/1993 | WIPO . |

OTHER PUBLICATIONS

"Anthroscopy Equipment and Supplies" (Instrument Makar).
"Ligament Screw System" (Biomet).
"The Complete Arthrex Information System" (Arthrex).
"MITEK GII Anchor" (Mitek Surgical Products).
"MITEK Anchor System" (Mitek Surgical Products).
"MITEK Quick Anchor" (Mitek Surgical Products).
"STATAK Soft Tissue Attachment Device" (Zimmer).
"TAG™ Tissue Anchor Guide System" (Acufex Microsurgical Inc.).
"Technique for Using the TAG™ Tissue Anchor—Rod Style" (Acufex Microsurgical Inc.).
"Technique for Using the TAG™ Tissue Anchor—Wedge Style" (Acufex Microsurgical Inc.).
"A Proposed Design for An Expanding Hip Nail" (Raftopoulos).
"Ligament Fastener Cuts Recovery Time" (Design News).

*Primary Examiner*—Sam Rimell

[57] ABSTRACT

A suture anchor includes a rivet for insertion into a predrilled bore hole in bone, and a setting pin which extends through an axial aperture in the rivet. Preferably the setting pin has barbed legs which are radially expandable to frictionally engage the walls of the bore hole to secure the anchor therein. The setting pin includes a suture accommodating aperture, surface, and/or slot. In one embodiment, a snap-fitting detent and notch are engageable with each other to form an escapement mechanism to position the setting pin at discrete positions within the axial aperture of the rivet.

18 Claims, 7 Drawing Sheets

U.S. PATENT DOCUMENTS

| | | |
|---|---|---|
| 4,632,100 | 12/1986 | Somers et al. . |
| 4,655,777 | 4/1987 | Dunn et al. . |
| 4,713,076 | 12/1987 | Draenert . |
| 4,738,255 | 4/1988 | Goble et al. . |
| 4,741,330 | 5/1988 | Hayhurst . |
| 4,760,843 | 8/1988 | Fischer et al. . |
| 4,790,304 | 12/1988 | Rosenberg . |
| 4,828,562 | 5/1989 | Kenna . |
| 4,870,957 | 10/1989 | Goble et al. ............................ 606/72 |
| 4,871,289 | 10/1989 | Choiniere . |
| 4,895,148 | 1/1990 | Bays et al. . |
| 4,898,156 | 2/1990 | Gatturna et al. . |
| 4,898,505 | 2/1990 | Froehlich . |
| 4,899,743 | 2/1990 | Nicholson et al. . |
| 4,921,383 | 5/1990 | Fischer . |
| 4,927,421 | 5/1990 | Goble et al. . |
| 4,946,468 | 8/1990 | Li . |
| 4,968,315 | 11/1990 | Gatturna . |
| 4,969,892 | 11/1990 | Burton et al. . |
| 4,976,680 | 12/1990 | Hayman et al. . |
| 5,002,550 | 3/1991 | Li . |
| 5,013,316 | 5/1991 | Goble et al. . |
| 5,037,422 | 8/1991 | Hayhurst et al. ..................... 606/74 X |
| 5,041,129 | 8/1991 | Hayhurst et al. . |
| 5,046,513 | 9/1991 | Gatturna et al. . |
| 5,053,047 | 10/1991 | Yoon . |
| 5,078,730 | 1/1992 | Li et al. . |
| 5,080,543 | 1/1992 | Murphy . |
| 5,084,050 | 1/1992 | Draenert . |
| 5,100,417 | 3/1992 | Cerier et al. ....................... 606/232 X |
| 5,102,421 | 4/1992 | Anspach, Jr. . |
| 5,156,616 | 10/1992 | Meadows et al. . |
| 5,167,664 | 12/1992 | Hodorek . |
| 5,176,682 | 1/1993 | Chow . |
| 5,207,679 | 5/1993 | Li . |
| 5,209,753 | 5/1993 | Biedermann et al. . |
| 5,217,486 | 6/1993 | Rice et al. . |
| 5,236,445 | 8/1993 | Hayhurst et al. . |
| 5,258,016 | 11/1993 | DiPoto et al. . |

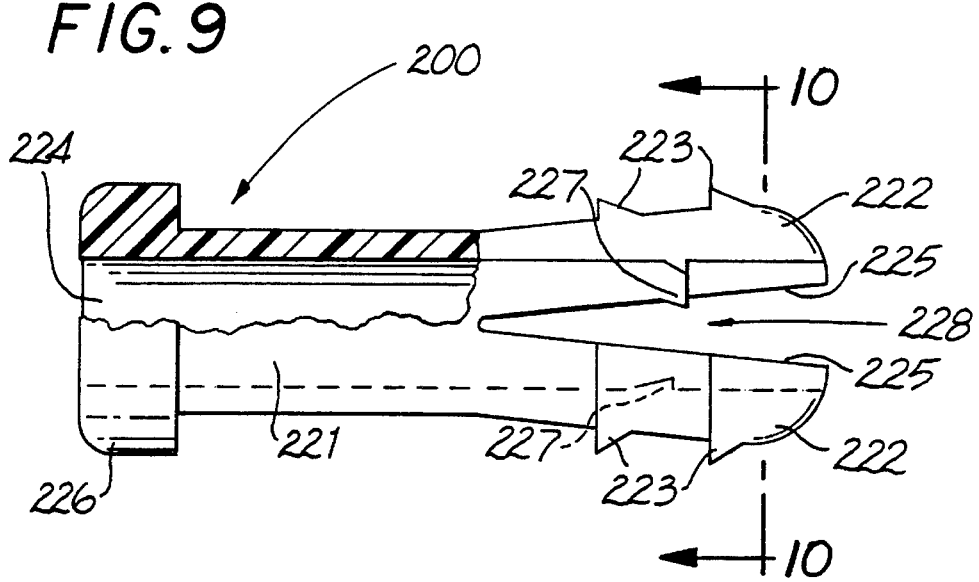
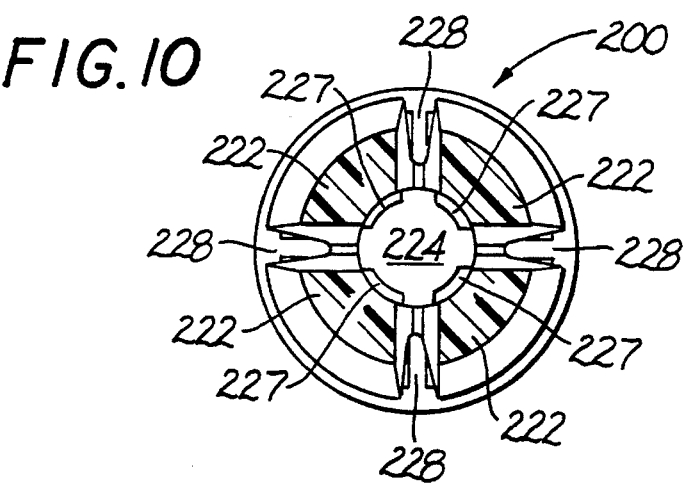
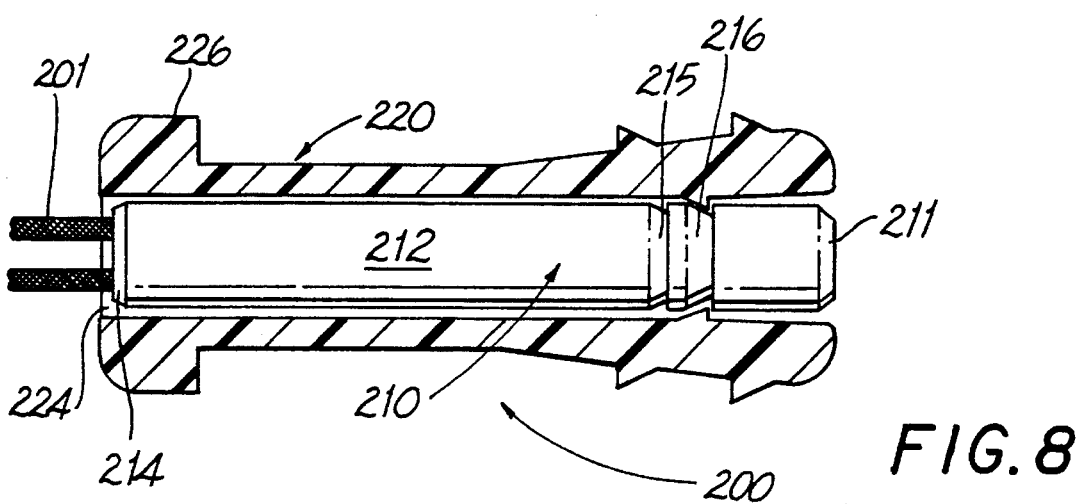

5,480,403

SUTURE ANCHORING DEVICE AND METHOD

This is a continuation of application Ser. No. 08/284,731 filed on Aug. 2, 1994, now abandoned which is a continuation of U.S. application 08/214,042 filed on Jan, 28, 1994, now abandoned, which is a continuation of U.S. application Ser. No. 07/898,799 filed on Jun. 15, 1992, now abandoned which is a continuation-in-part of U.S. application Ser. No. 07/673,953 filed on Mar. 22, 1991, now abandoned.

BACKGROUND OF THE INVENTION

1. Field of the Invention

This invention relates to a method and apparatus for anchoring a suture, and more particularly to a suture anchor insertable into a preformed hole in bone.

2. Background of the Art

Suture anchors are used in various types of orthopedic surgery to secure sutures to bone. Typically, the suture anchor is implanted into a hole predrilled into a bone mass. The suture anchor may be employed, for example, to anchor ligaments or tendons to the bones in the knee, shoulder, and elbow, and is especially useful in joint reconstruction and arthroscopic surgery.

Various types of suture anchors are known. For example, U.S. Pat. No. 5,037,422 to Hayhurst et al. discloses an anchor for securing a suture to a bore hole in a bone. The suture anchor includes an elongated body having a tip at a distal end of the body. Two slots extend lengthwise at spaced locations on the body. The suture is attached to the tip. The anchor possesses a ridge which engages the wall of the bore hole and lodges more firmly when the suture is pulled. Other sutures anchoring devices are disclosed in U.S. Pat. Nos. 4,632,100; 5,041,129; 5,046,513; 4,898,156; 4,899,743; and 4,946,468.

Generally it is desirable that the suture anchor be easily implanted, yet firmly lodged within the bore hole in the bone to resist pull-out of the suture. Also, the suture anchor must be fabricated from a biocompatible material to avoid undesirable body tissue reaction.

SUMMARY OF THE INVENTION

A suture anchor is provided herein for anchoring a suture to bone during a surgical procedure. The suture anchor comprises a rivet for insertion distally into a pre-drilled hole in bone or hard tissue, the rivet including a body portion having a distal end and an axially extending aperture, and at least two legs extending proximally from the body portion. The legs are radially expandable in response to proximal movement of a setting pin. The suture anchor also includes a setting pin slidably disposed through the axially extending aperture. The setting pin has suture attachment means, and is movable between a distal position with respect to the rivet wherein the rivet legs are not expanded, and a proximal position with respect to the rivet wherein the rivet legs are urged to a radially expanded configuration.

In an alternative embodiment, an escapement feature is included to prevent extraction of the pin from the anchor and to position to the pin at any one of discrete intervals within the rivet. In this embodiment, the pin is moved distally to activate the suture anchor. In yet another embodiment, a unique matching cross section of the pin and rivet aperture are employed to prevent suture interference with the setting action by locating the suture between the legs of the rivet.

The suture anchor may be fabricated of a biodegradable material.

BRIEF DESCRIPTION OF THE DRAWINGS

FIG. 8 is a partly sectional side view showing an alternative embodiment of the suture anchor in activated condition.

FIGS. 9 and 10 illustrate, respectively, partly sectional side and end views of an alternative embodiment of the rivet.

DETAILED DESCRIPTION OF PREFERRED EMBODIMENT(S)

The invention described herein is a repair device to be used in surgical procedures where there is a need to attach soft tissue to bone using sutures. The implantable device secures the suture to a hole formed in the bone. The device is intended to facilitate repair, provide stable anchorage of soft tissue, restore function, reduce the possibility of complications, and increase the success of the repair procedure. The two component device consists of a radially expandable rivet and a suture accommodating set pin. Functionally, the rivet portion consists of a cylinder which contains at least two and preferably four legs with a tapered cross section which, when forced outward, expand to lock the device inside an appropriately sized hole. The legs also have ridges providing barb structures which actively anchor the device in bone and act to prevent the device from being pulled out.

The setting pin portion, when moved into the rivet, acts to expand the rivet's legs. The pin also provides a means for attaching one or more sutures to the pin. In an exemplary embodiment, this may be accomplished through a suture accommodating hole(s) or groove(s) in the pin and, these features may be oriented transversely or longitudinally. In an exemplary embodiment, the set pin has an approximately sized conical head which functions to aid insertion into a constant diameter hole and to act as a stop to indicate when the device is fully engaged. In an exemplary embodiment, the pin may also possess a unique cross section, which when combined with an appropriately configured hole in the rivet, restricts longitudinal pin orientation. Orientation allows the suture(s) to be located in the slots between the rivet legs and prevents suture interference with the setting action.

The suture-rivet is used by first drilling an appropriately sized hole in the bone. The suture-rivet can be preloaded with suture or it can be loaded with suture at the time of surgery. The device is inserted into the bone hole using a complementary application instrument. The insertion device limits the depth at which the suture-rivet can be inserted. The insertion device is removed which leaves the device in the bone hole. This is accomplished due to the mechanical interference of the rivet ridges with the walls of the bone hole. In an exemplary embodiment, the suture exiting the hole is pulled (tensioned) to set the pin. This pulling action is in the same direction as that applied to the device under load. Higher tensile loads result in greater anchoring forces by increasing radial expansion of the rivet legs. An active anchoring system is preferred for this type of device.

A more detailed description of exemplary embodiments is given below, wherein the term "distal" refers to the direction in which the rivet is implanted, i.e., towards the interior of the bone, and the term "proximal" refers to a direction away from the bone, i.e., opposite to the distal direction.

Figure 1:
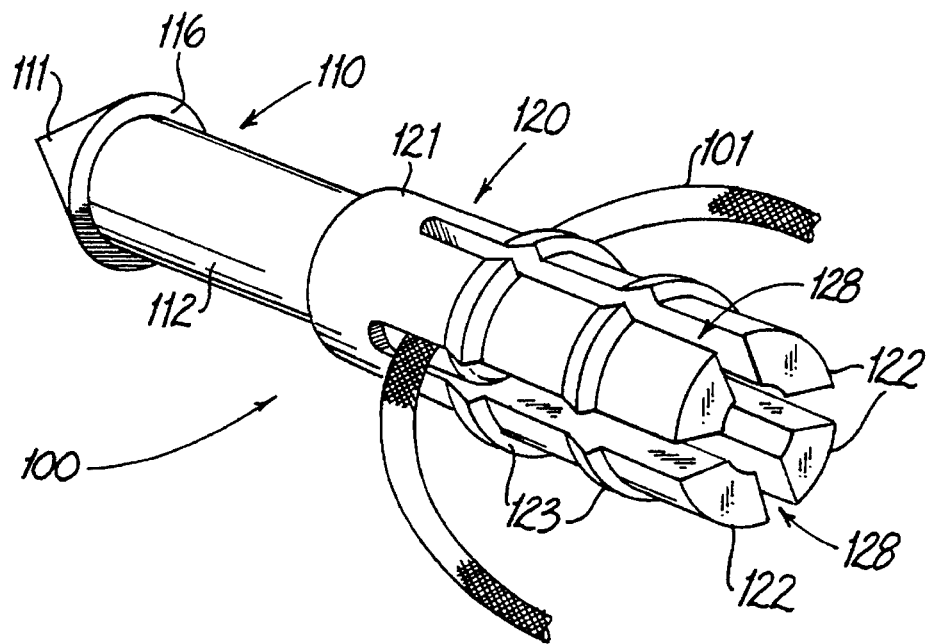
FIG. 1 is a perspective view of the suture anchor of the present invention.
Figure 3:
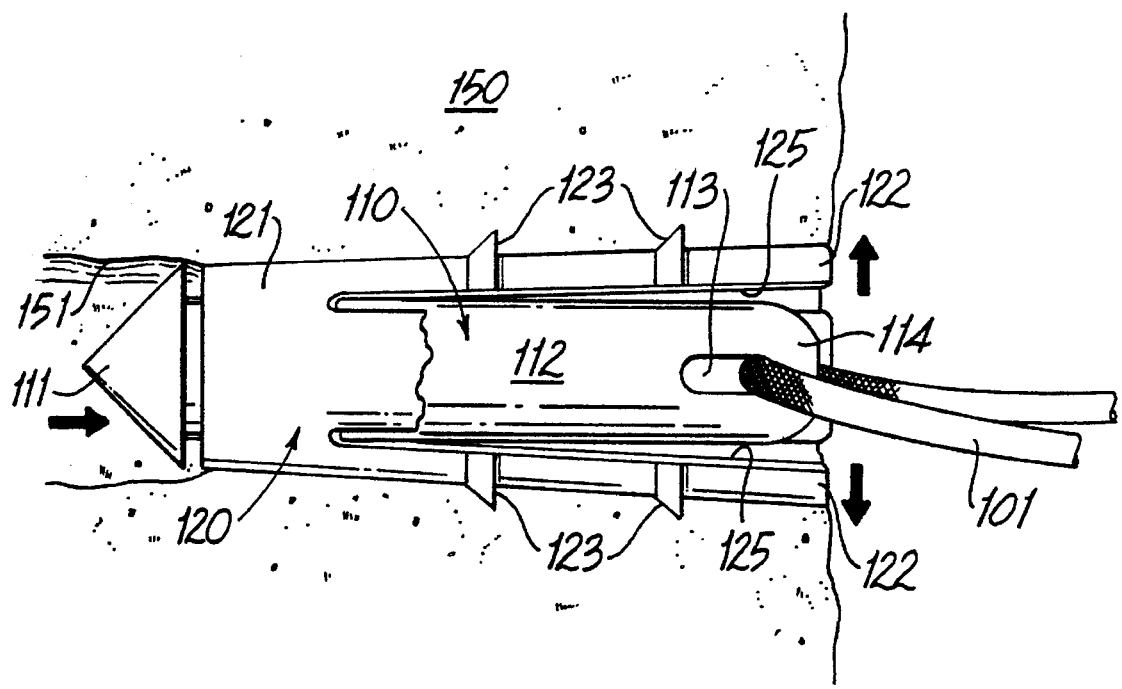
FIG. 3 is a side view showing the suture rivet implanted in bone and activated.
Figure 2:
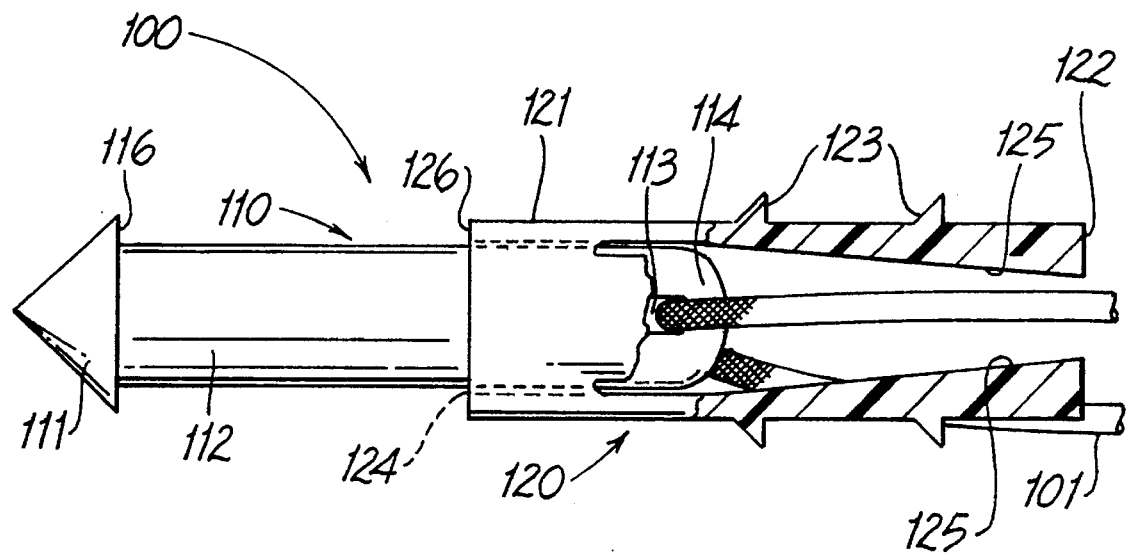
FIG. 2 is a partially cut away side view of the suture anchor in inactivated condition.

Referring to FIG. 1, a suture anchor 100 is illustrated in perspective. FIG. 2 shows a partly cut-away side view of suture anchor 100. FIG. 3 shows the suture anchor implanted in bone and "activated", i.e. the legs of the suture anchor are expanded for gripping the walls of the bore hole into which the suture anchor 100 is implanted.

Suture anchor 100 includes a rivet 120 and a setting pin 110, which is slidably disposed through an axial aperture in the rivet 120. Setting pin 110 includes a distal tip 111 which may optionally be terminated in a sharp point, a generally cylindrical shaped body portion 112, a proximal end 114 which is preferably tapered or rounded, and an aperture 113 for receiving a suture 101 to be anchored. The aperture 113 can be oriented transverse to the longitudinal axis of the setting pin as is shown in FIG. 1.

An alternative embodiment of the setting pin is illustrated in perspective side, front and rear end views, in FIGS. 4, 5, 6 and 7, respectively. Alternative embodiment 130 includes a distal tip portion 131 tapering to a flat frontal surface 136, and having a rear, or proximal, abutment surface 136A. Pin 130 further includes a shaft portion 132 and a tapered or rounded proximal or rear portion 134. Shaft portion 132 includes at least one, and preferably two suture accommodating slots 135 extending longitudinally along opposite sides of the pin 130. A suture accommodating aperture 133 extends transversely to the longitudinal axis of the pin 130 and is located in proximity to the distal end of the pin. The suture can be prethreaded through aperture 133 and disposed within slots 135 prior to assembly of the pin 130 and rivet 120. In the description below, rivet 120 is discussed in conjunction with pin 110. However, it should be recognized that pin 130 can be substituted for pin 110 and is equally suitable for use in conjunction with rivet 120.

The rivet 120 includes a body portion 121 through which an axial aperture 124 extends for receiving the setting pin 110. Rivet 120 also possesses at least two, and preferably four, legs 122, which extend proximally from the body portion 121. The legs 122 are separated by notches 128 and are resiliently movable in a radial direction. Each leg 122 has an inner camming surface 125 which is inclined towards the axial center of the rivet such that proximal movement of the setting pin 110 causes the proximal end 114 to cam against the inner surface 125 of the leg, thereby urging the leg 122 radially outward. The outer surfaces of the legs possess proximal pointing barbs 123 to grip the inner walls of the bore hole in the bone.

In use, the setting pin 110 is slidably disposed through aperture 124 in rivet 120. The suture 101 to be fastened is disposed through lateral aperture 113 in the setting pin and may be knotted to secure it to the setting pin for anchoring. In the "inactivated" configuration, the setting pin 110 is in a position such that it is relatively distally advanced with respect to the rivet 120. The suture anchor 100 is distally advanced into a predrilled bore hole 151 in a bone 150. To "activate" the suture anchor the setting pin 110 is moved proximally with respect to the rivet 120. This may be accomplished by pulling the suture 101, whereupon the proximal end 114 of the setting pin cams against the inner surfaces 125 to urge legs 122 radially outward, as illustrated in FIG. 2. The barbs 123 then frictionally engage the walls of the bore hole and resist proximal movement of the rivet 120. Thus, suture anchor 100 is locked into place for firmly securing the suture 101. The distal end portion 111 of the setting pin has a proximally facing abutment surface 116, and the body portion 121 of the rivet has a distally facing abutment surface 126. Abutment surfaces 116 and 126 cooperate to limit the proximal movement of the setting pin 110. Thus, when the setting pin 110 is moved to its most proximal position with respect to the rivet 120, surfaces 116 and 126 abut each other and thereby prevent the setting pin from being pulled proximally out of the rivet 120 by pulling force exerted on the suture 101. Tension exerted on the suture 101 serves to more tightly lodge the suture anchor 100 within the bore hole.

The suture anchor of this embodiment and the alternative embodiments described below are preferably fabricated from a flexible and resilient material with a strength sufficient for the purposes described herein. The suture anchor can be fabricated from bioabsorbable materials such as homopolymers and copolymers of glycolide, lactide, dioxanone, caprolactone, trimethylene carbonate, and mixtures thereof.

FIGS. 8 to 14 are directed to an alternative embodiment 200 of the suture anchor of the present invention.

Referring to FIGS. 8, 9, 10 and 11, suture anchor 200 includes rivet 220 and setting pin 210, which is slidably disposed through axial aperture 224 in the rivet 220. Setting pin 210 includes a distal tip 211, which may have a circumferential tapered portion to facilitate insertion of the pin through axial aperture 224 in the rivet. Setting pin 210 further includes a cylindrical body portion 212 and a proximal end 214 at which sutures 201 are attached.

Figure 11:
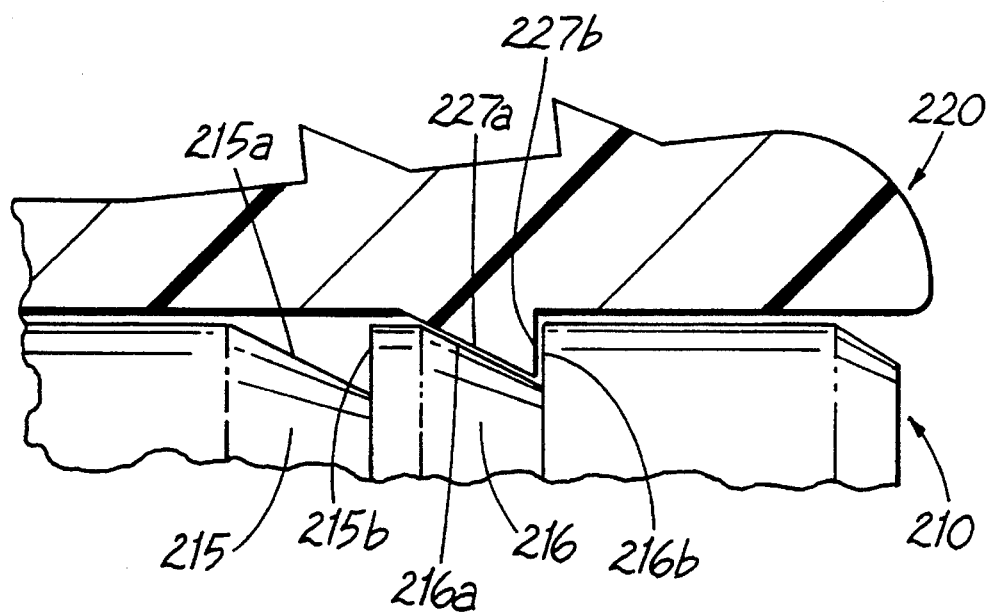
FIG. 11 is a more detailed partly sectional view of the locking feature of the present invention.
Figure 4:
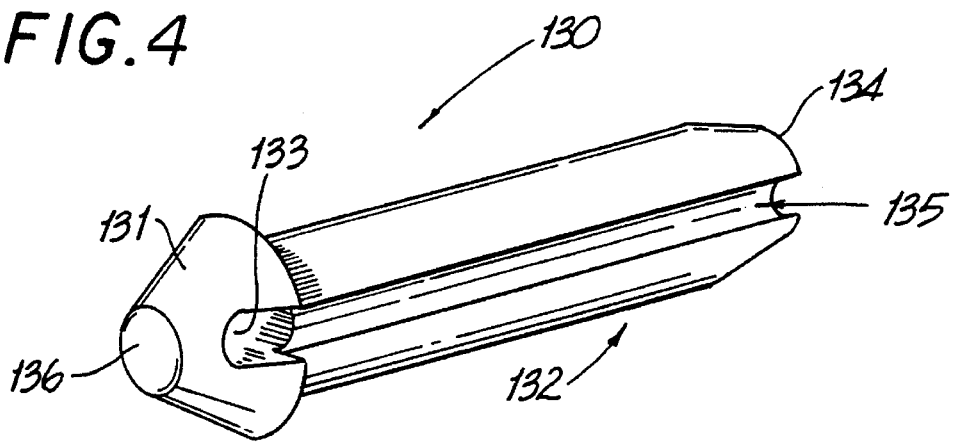
FIGS. 4 to 7 shows, respectively, perspective, side, front end, and rear end views of an alternative embodiment of the pin.
Figure 5:
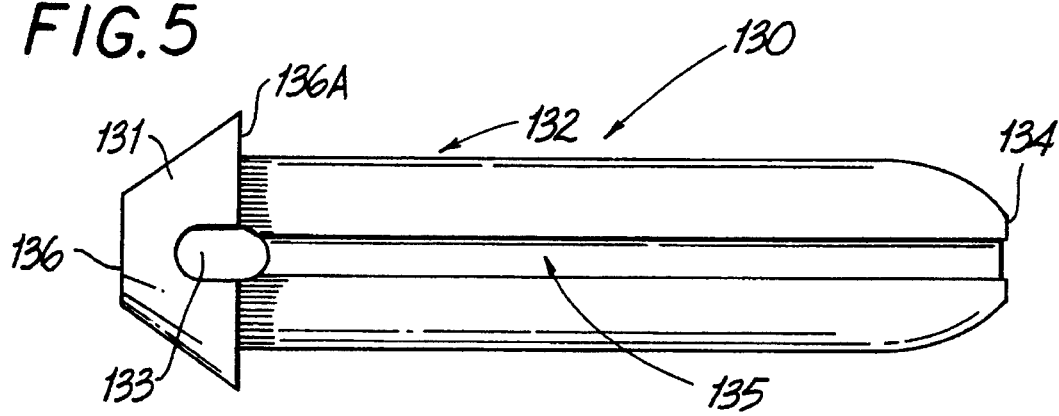
Figures 6, 7:
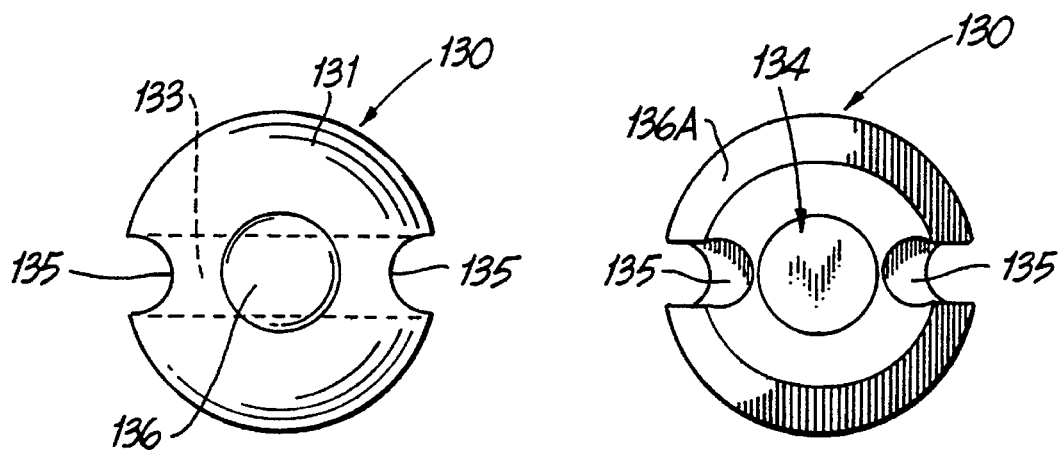

An escapement feature is incorporated into the suture anchor 200. Setting pin 210 includes at least one, and preferably two or more circumferential notches 215 and 216. Referring to FIG. 11, each notch has an inclined proximal surface 215a and 216a, respectively, and a distal abutment surface 215b and 216b, respectively. Notches 215 and 216 are configured and dimensioned so as to engage corresponding detents in the rivet, as discussed below.

Referring to FIGS. 8, 9, 10 and 11, the rivet 220 is illustrated in its activated, or expanded condition. Rivet 220 includes body portion 221, proximal head portion 226, and axial aperture 224 extending through the rivet 220 for receiving the setting pin 210. Rivet 220 also possesses at least two, and preferably four, legs 222, which extend distally from the body portion 221 and which are separated by slots 228. Legs 222 are resiliently movable in a radial direction and each has an inner camming surface 225 which is inclined towards the axial center of the rivet such that distal movement of the setting pin 210 causes the distal end 211 to cam against the inner surfaces 225 of the legs, thereby urging the legs 222 radially outward. The outer surfaces of the legs possess proximal pointing barbs 223 to grip the inner walls of the bore hole in the bone.

The rivet legs each further include inner detents 227 which are configured and dimensioned so as to be engageable with notches 215 and 216 of the setting pin. Detents 227 include an inclined proximal surface 227a and a distal abutment surface 227b, as is seen more clearly in FIG. 11.

In use, the rivet 220 is implanted in a predrilled bore hole in a bone. the bore hole is preferably of such diameter to accommodate the body portion 221 and legs 222. The proximal head portion 226 remains outside the bone. After the rivet 220 is implanted, the setting pin 210 is inserted into aperture 224 in the rivet. As the setting pin 210 is moved distally through aperture 224, the distal edge 211 of the setting pin cams the inner surface 225 of the legs, thereby urging the legs 22 to expand radially outward and moving the barbs 223 into frictional engagement with the wall of the bore. When notch 216 of the setting pin is moved up to detent 227, the notch and detent engage each other to form a snap-fit locking mechanism. Once the detent 227 and notch 216 snap together, the setting pin 210 cannot easily be removed, i.e., it is locked with respect to the proximal direction. An attempt to move the setting pin 210 proximally out of the rivet 220 will cause surfaces 227b and 216b to abut each other thereby resisting extraction of the setting pin 210 from the rivet 220. Although proximal movement is prevented by the snap lock feature, inclined surface 227a and 216a can slide along each other to permit further distal movement of the setting pin 210. Thus setting pin 210 can be advanced further to engage the second notch 215 with the detent 227. The second notch 215 engages and cooperates with the detent 227 in the same manner as the notch 216. A series of notches such as 215, 216, and others if desired, thereby also act as an indexing means to position the setting pin 210 at discrete intervals within the rivet 220 for anchoring suture 201.

Figure 12:
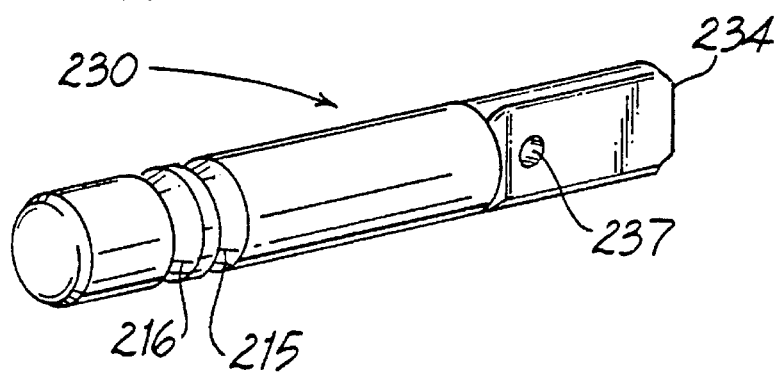
FIGS. 12 to 14 show, respectively, perspective, plan and elevational views of an alternative embodiment of the rivet.
Figure 13:
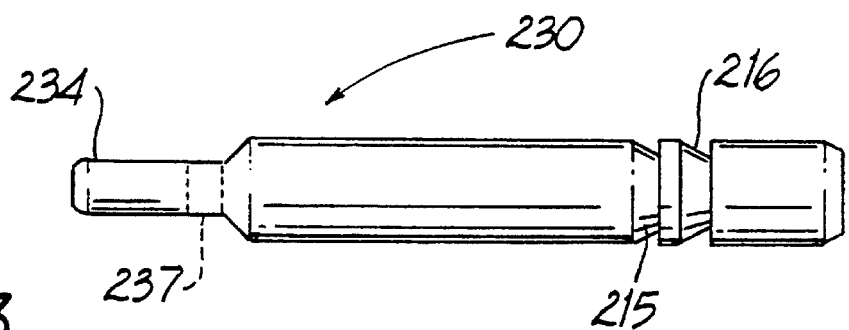
Figure 14:
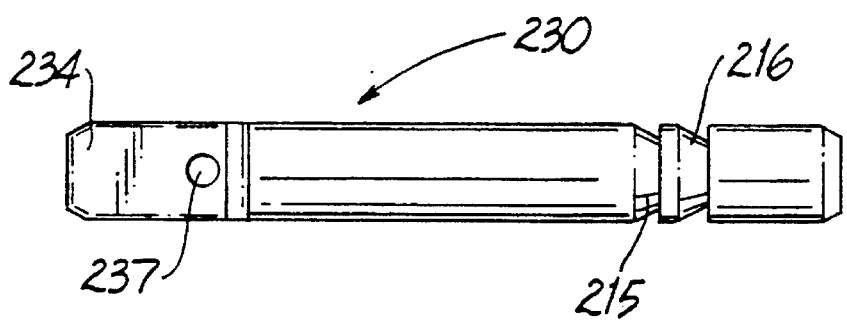
Figure 15:
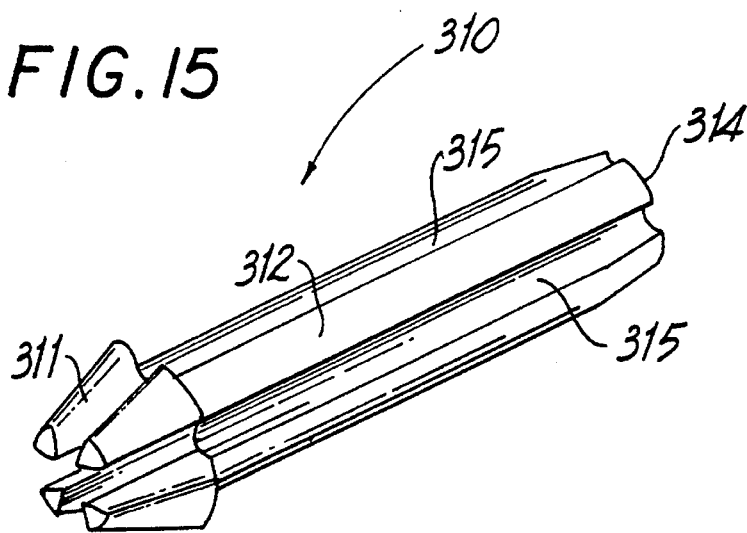
FIGS. 15 to 18 are, respectively, perspective, side elevational, front end and rear end views of another embodiment of the pin.
Figure 16:
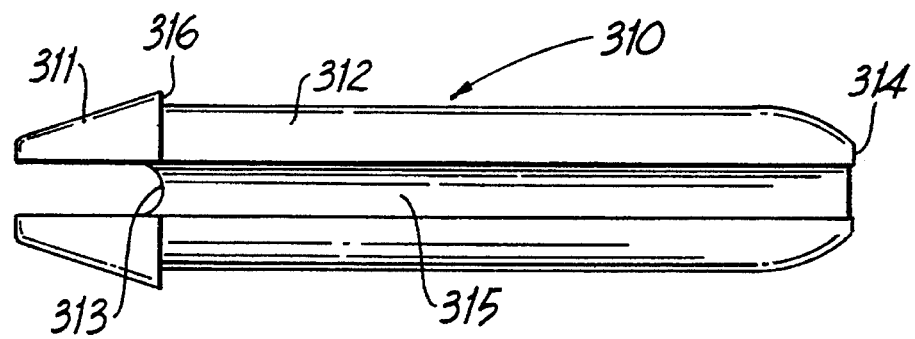
Figure 17:
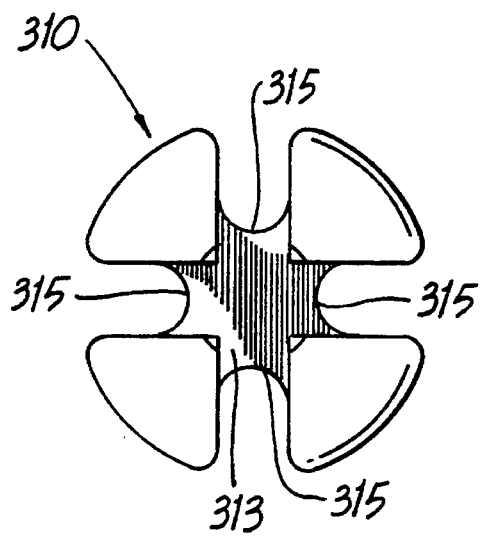
Figure 18:
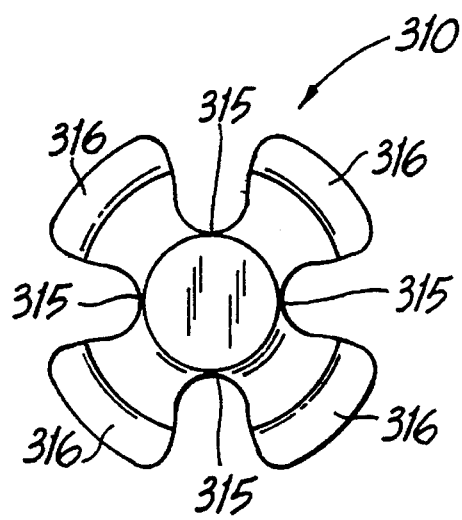
Figure 19:
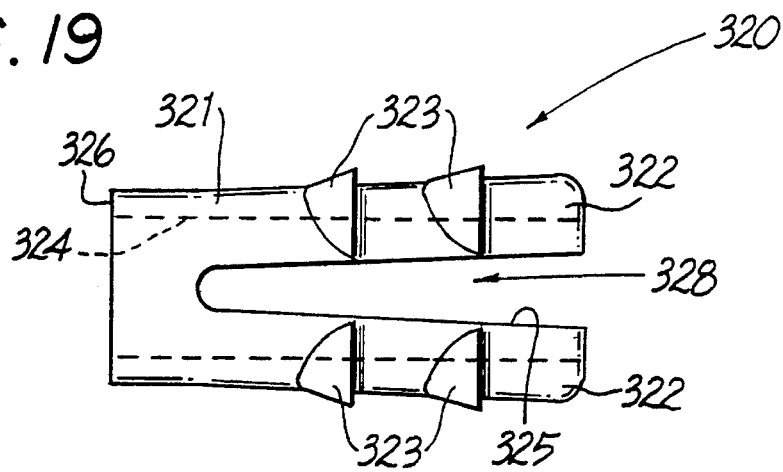
FIGS. 19 to 22 are, respectively, side elevational, front end, rear end and sectional view of another embodiment of the rivet.
Figure 20:
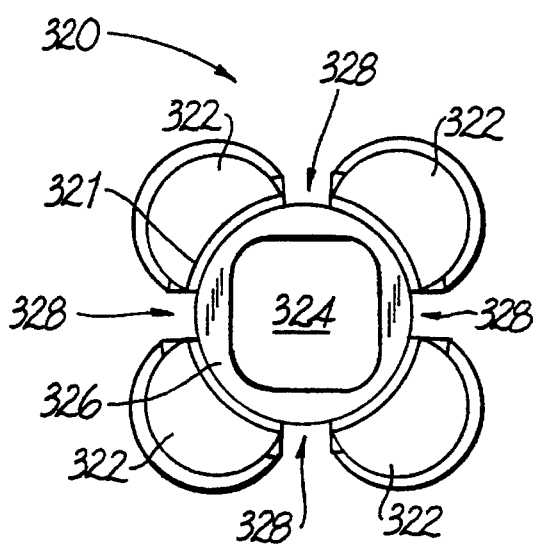
Figure 21:
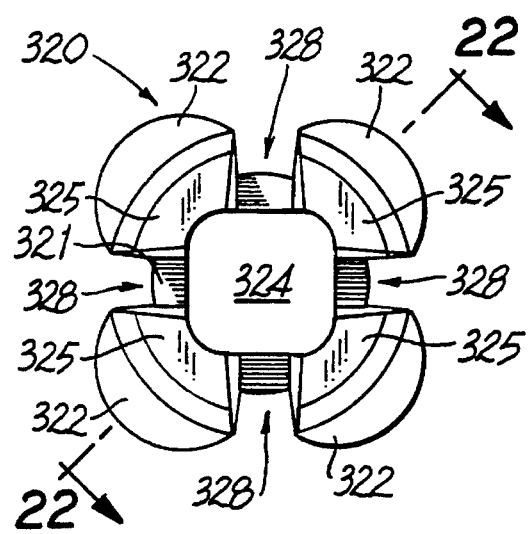
Figure 22:
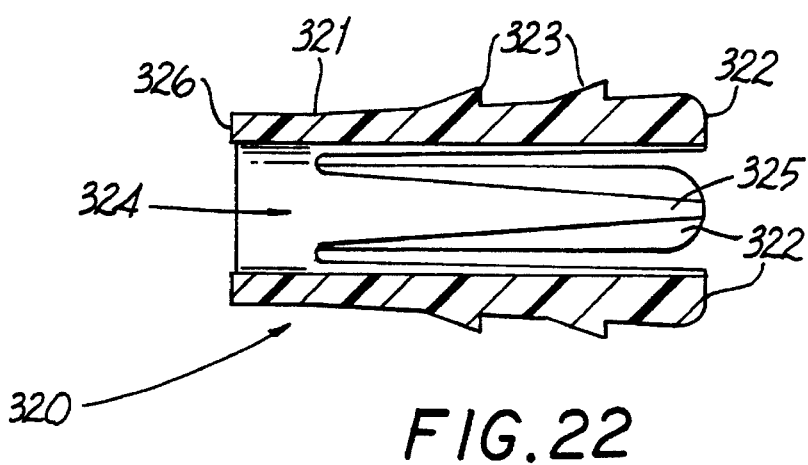

Pin 210 is shown with suture 201 affixed to the proximal end 214. An alternative embodiment of the pin is shown in FIGS. 12 to 14. Embodiment 230 of the pin is similar to pin 210 except that the proximal rear section 234 is a narrowed and flattened portion with a suture accommodating aperture 237 extending laterally therethrough in a direction transverse to the longitudinal axis of the pin 230. The flattened portion 234 allows space for the suture to extend therealong.

FIGS. 15 to 18 show an alternative embodiment of a pin 310 which includes at least two and preferably four suture accommodating slots 315 extending along the body portion 312. A suture holding surface 313 is located at the distal end of the body portion 312. Slots 315 divide the tip 311 into four clover leaf type sections which each have a proximal abutment surface 316. As with the other pin embodiments, a tapered proximal rear section 314 facilitates spreading of the rivet legs when the suture anchor is activated. In use, a suture is simply placed along two of the slots 315 and across the suture holding surface 313.

FIGS. 19 to 22 disclose another embodiment, 320, of the rivet shown in the expanded or activated condition. Rivet 320 includes a body portion 321 at least two and preferably four legs 322 extending axially through the rivet 320 for slidably receiving a setting pin, such as pin 310. The legs 322 are divided by notches 328 and are configured in a lobate pattern as can be seen from end views FIG. 20 and FIG. 21. Barbs 323 extend outwardly from the outer surface of the legs 322 and, as described for the previously mentioned embodiments, grip the inner walls of the hole in the bone into which the rivet 320 is implanted. The legs 322 each possess an inner facing camming surface 325 which is inclined towards the axial center of the aperture 324. Thus, when setting pin 310 is positioned in the aperture 324 and is moved proximally, the proximal end cams against surfaces 325 and spreads the legs 322 radially outward to set the rivet 320 within the bore in the bone. Setting pin 310 may be pulled proximally by the suture until the stop surface 316 abuts the distal stop surface 326 of the rivet.

It should be noted that the body portion 312 and the axial aperture 324 can have a unique matching cross section (illustrated as a generally squared-off shape in FIG. 18, 20 and 21) to prevent rotation of the pin 310 within rivet 320, thereby orienting the pin 310 within aperture 324 such that the suture is located between legs 322 to prevent interference with the setting or activation of the rivet 320.

The present device has the significant advantage of providing an easy, time saving technique and device for soft tissue attachment to bone. The most unique aspect of the device is its self-tightening means of providing anchorage. This active means of anchorage is designed to provide greater pull out strength as the tension on the suture increases. Installation requires a hole to be drilled in bone, the device inserted into the hole, and the device set or tightened with a pull on the suture. Another advantage is that the device is designed to be inserted arthroscopically through an 8 mm cannula. The device provides sufficient anchoring strength to allow repair to occur concurrently with a partial return to full function. The device is primarily subjected to tensile forces and provides adequate strength to stabilize the reattached soft tissue. By fabricating the device out of a biodegradable material, the device is capable of providing full initial anchorage strength, and, with time, allows for gradual load sharing to the repaired tissue. This load sharing capability may be the optimal means for achieving full repair and restoration of function. Another advantage is that the resorbable material will eventually be replaced by natural tissue.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A suture anchor, comprising:
   a rivet for insertion distally at least partially into a hole in bone, said rivet including a body portion having a distal end and an axially extending aperture, and at least two legs extending proximally from said body portion, said legs being radially expandable in response to proximal movement of a setting pin;
   b) a setting pin for slidable positioning through said axially extending aperture, said setting pin having means for holding a suture, said setting pin being movable between a distal position with respect to said rivet wherein said rivet legs are not expanded, and a proximal position with respect to said rivet wherein said rivet legs are urged to a radially expanded configuration, said means for holding a suture being located in proximity to the distal end of said setting pin, and said setting pin further comprising at least two suture accommodating slots extending longitudinally along the sides of said setting pin; and
   c) means for preventing rotation of the setting pin within said axially extending aperture, wherein said rivet legs are spaced apart from each other and said suture accommodating slots are aligned with the space between the legs of the rivet.

2. The suture anchor of claim 1, wherein the suture anchor is fabricated from a bioabsorbable material.

3. The suture anchor of claim 2, wherein said bioabsorbable material is a polymer selected from the group consisting of homopolymers and copolymers of glycolide, lactide, caprolactone, dioxanone, trimethylene carbonate and mixtures thereof.

4. The suture anchor of claim 1, wherein said rivet further possesses at least one barb on the outer surface of each leg.

5. The suture anchor of claim 1, wherein said means for holding a suture comprises a suture receiving aperture extending laterally through nail setting pin.

6. The suture anchor of claim 1, wherein said setting pin and said rivet each include stop surfaces for abutting each other to prevent further proximal movement of the setting pin relative to the rivet when the setting pin has been moved to a predetermined position.

7. The suture anchor of claim 1, wherein a portion of the surface of said setting pin comprises a non-circular transverse cross-section and a portion of the surface of said axially extending aperture has a non-circular transverse cross-section, said portion of said setting pin surface contacting said portion of said axially extending aperture surface, thereby oftenting said setting pin within said axially extending aperture to prevent rotation of said setting pin within said axially extending aperture.

8. The suture anchor of claim 1, wherein said rivet legs each include an inner camming surface for contact with the proximal end of the setting pin said camming surface being inclined towards the axial center of the rivet.

9. A suture anchor comprising:

a rivet for insertion distally into a hole in bone, said rivet including a body portion having a distal end and an axially extending aperture defining an inner surface, a head portion proximal to the body portion and having a wider diameter than said body portion, and at least two legs extending distally from said body portion, said legs being radially expandable in response to distal movement of a setting pin through said aperture;

a setting pin for slidable positioning through said axially extending aperture, said setting pin having means for holding a suture, and said setting pin being movable between a proximal position with respect to said rivet wherein said rivet legs are not expanded, and a distal position with respect to said rivet wherein said rivet legs are urged to a radially expanded configuration; and, escapement means for preventing movement of the setting pin when it has reached any one of one or more discrete location with respect to said rivet.

10. The suture anchor of claim 9, wherein the suture anchor is fabricated from a bioabsorbable material.

11. The suture anchor of claim 10, wherein said bioabsorbable material is a polymer selected from the group consisting of homopolymers and copolymers of glycolide, lactide, caprolactone, dioxanone, trimethylene carbonate, and mixtures thereof.

12. The suture anchor of claim 9, wherein said rivet further possesses at least one barb on the outer surface of each leg.

13. The suture anchor of claim 9, wherein said means for holding a suture comprises a suture receiving aperture extending laterally through said setting pin.

14. The suture anchor of claim 13, wherein said suture receiving aperture is located in proximity to the proximal end of said setting pin.

15. The suture anchor of claim 9, wherein said rivet legs each include an inner camming surface for contact with the proximal end of the setting pin said camming surface being inclined towards the axial center of the rivet.

16. The suture anchor of claim 9, wherein said escapement means comprises a detent located on one of said setting pin or rivet, and a corresponding notch located on the other of said setting pin or rivet, the detent being resiliently engageable with said notch.

17. The suture anchor of claim 16, wherein said detent and notch are configured and dimensioned to permit distal movement of the setting pin with respect to the rivet, but to resist proximal movement of the setting pin with respect to the rivet.

18. The suture anchor of claim 17, wherein said escapement means includes a series of spaced apart notches located on said setting pin, and at least one corresponding detent on the inner surface of said rivet.

* * * * *